United States Patent [19]

Hofen et al.

[11] Patent Number: 5,866,721

[45] Date of Patent: Feb. 2, 1999

[54] PROCESS FOR SEPARATING THE PRODUCT GAS MIXTURE FROM THE CATALYTIC SYNTHESIS OF METHYL MERCAPTAN

[75] Inventors: Willi Hofen, Rodenbach; Wolfgang Boeck, Langenselbold; Stephan Rautenberg, Hanau; Joerg Sauer, Rodenbach; Dietrich Arntz, Oberursel; Ralf Goedecke, Rodenbach; Wolfgang Taugner, Altenstadt; Raymund Sonnenschein, Alzenau, all of Germany

[73] Assignee: Degussa Aktiengesellschaft, Frankfurt am Main, Germany

[21] Appl. No.: 885,043

[22] Filed: Jun. 30, 1997

[30] Foreign Application Priority Data

Dec. 27, 1996 [DE] Germany ................. 196 54 516.1

[51] Int. Cl.⁶ .................................................. C07C 319/06
[52] U.S. Cl. ........................... 568/71; 423/220; 423/226; 203/96; 203/76
[58] Field of Search .............................. 568/71; 423/220, 423/226; 203/96, 76

[56] References Cited

FOREIGN PATENT DOCUMENTS 2477538  9/1981  France .
17686826  8/1971  Germany .

*Primary Examiner*—Gary Geist
*Assistant Examiner*—Jean F. Vollano
*Attorney, Agent, or Firm*—Beveridge, DeGrandi, Weilacher & Young, L.L.P.

[57] ABSTRACT

A process for separating the product gas mixture from the catalytic synthesis of methyl mercaptan. Because of improved separation of the product gas mixture into its components, less hydrogen sulfide and methyl mercaptan are lost in discharging the inert gases than in the known process. The inert gases can be burned without aftertreatment of the exhaust gas. Likewise, the process water that is discharged is less contaminated with polysulfides.

10 Claims, 2 Drawing Sheets

PROCESS FOR SEPARATING THE PRODUCT GAS MIXTURE FROM THE CATALYTIC SYNTHESIS OF METHYL MERCAPTAN

INTRODUCTION AND BACKGROUND

The present invention relates to a process for separating the product gas mixture from the catalytic synthesis of methyl mercaptan from hydrogen sulfide and methanol. The product gas mixture has a temperature of 100° C. to 150° C. and a pressure of 6 to 12 bar. It contains not only the desired methyl mercaptan but also the water produced in the reaction, the byproducts dimethyl sulfide and dimethyl ether and small proportions of polysulfides, as well as unreacted methanol, excess hydrogen sulfide, and the gases nitrogen, carbon dioxide, carbon monoxide and hydrogen, which are inert in this reaction. Separation of the product gas mixture into its components recovers methyl mercaptan and dimethyl sulfide, removes water and the inert gases, and recycles the unconsumed methanol and hydrogen sulfide to the synthesis reactor.

Methyl mercaptan is an important industrial intermediate for the synthesis of methionine and for production of dimethyl sulfoxide and dimethyl sulfone. At present it is produced predominantly from methanol and hydrogen sulfide by reaction in the presence of an aluminum oxide catalyst. Methyl mercaptan is usually synthesized in the gas phase at temperatures from 300° C. to 500° C. and at pressures from 1 to 5 bar. The catalyst is usually doped with potassium tungstate as an activator to increase its activity and selectivity. The reaction of hydrogen sulfide and methanol to produce methyl mercaptan is an exothermic process which releases 28,500 kJ per kmol methanol reacted.

The whole process of methyl mercaptan production can be divided into two parts. The first part includes pretreatment of the feed gas mixture and its conversion to methyl mercaptan. The second part includes the separation of the product gas mixture to recover methyl mercaptan, recycling of unconsumed methanol and hydrogen sulfide, and disposal of wastewater and waste gases. This invention relates to improvements in the second part of the production process.

German Patent 17 68 826 describes a process for separating the product gas mixture from methyl mercaptan synthesis, in which the product gas is distilled at a pressure not greater than 11 bar and a temperature of 10° C. to 140° C. The gaseous phase in this distillation consists essentially of hydrogen sulfide, inert gases, dimethyl sulfide and methyl mercaptan. Methyl mercaptan and dimethyl sulfide are washed out of the gas phase with a countercurrent stream of methanol. The remaining hydrogen sulfide and the inert gases are returned to the synthesis reactor as recycle gas. The wash methanol carrying methyl mercaptan and dimethyl sulfide is redistilled along with the distillation bottoms, which are practically free of hydrogen sulfide, and is also returned to the production process.

The methyl mercaptan which can be obtained by this process still contains up to 0.015% by weight hydrogen sulfide and up to 0.15% by weight methanol as minor impurities.

Some of the inert gases enter the production process as impurities in the hydrogen sulfide make-up gas. Inert gases also form due to decomposition of methanol in the synthesis reactor. According to German Patent 17 68 826, part of the hydrogen sulfide recycle gas is discharged and burned to avoid accumulation of the inert gases in the process. Valuable hydrogen sulfide gas is lost to the process by doing that.

The sulfur dioxide formed in the burning must be removed from the exhaust gas to meet current exhaust gas standards.

The water formed in the synthesis of methyl mercaptan is used, after it is separated from the product gas mixture, to break the methyl mercaptan/methanol and dimethyl sulfide/methanol azeotropes. Finally, the water must be removed continuously from the process. Here, there is a significant problem in that the methyl mercaptan, dimethyl sulfide and polysulfides must be removed as completely as possible from the wastewater to prevent odorous emissions and environmental damage.

According to French Patent 2 477 538, the product gas mixture, after leaving the reactor, passes through two condensation stages to condense most of the gas mixture. The condensate is collected at a pressure of 7 bar and a temperature of 30° C. in a phase separation tank for separation into an organic phase and an aqueous phase. The uncondensed gases rich in hydrogen sulfide are washed with methanol and then removed from the process for burning. The wash liquid is likewise collected in the phase separation tank. The organic and aqueous phases from the phase separation tank are further processed separately in distillation columns.

One problem with the technology known at the current state of the technology is the fact that the product gas mixture is not separated sharply enough into the separate streams of materials. The result is, for example, that methyl mercaptan is also recycled into the synthesis reactor along with the hydrogen sulfide recycle gas, and the inert gases removed for burning still contain high proportions of hydrogen sulfide, methyl mercaptan and methanol. Furthermore, the water being removed from the process is not pure enough to be discharged without further treatment. Very generally, this inadequate separation of the material streams causes higher power costs, as greater material flows must be recycled. Burning of valuable reactants (hydrogen sulfide, methanol) and the consequential post-treatment of the exhaust gas also incur high costs.

One object of this invention, therefore, is to separate the product gas mixture from methyl mercaptan synthesis to obtain improved separation of the product gas mixture into the individual material streams.

SUMMARY OF THE INVENTION

The above and other objects of the invention are attained by a process for separation of the product gas mixture from the catalytic synthesis of methyl mercaptan from hydrogen sulfide and methanol, which is produced at a temperature of 100° C. to 150° C. and a pressure of 6 to 12 bar, into the components methyl mercaptan, dimethyl sulfide, polysulfides, water, methanol, hydrogen sulfide and inert gases, comprising the following process steps:

a) separation of the product gas stream into an aqueous condensate containing methanol and water and an organic condensate containing hydrogen sulfide, methyl mercaptan and dimethyl sulfide, and into a residual gas stream containing hydrogen sulfide and methyl mercaptan, by a two-stage partial condensation in which the aqueous condensate is condensed at temperatures from 55° C. to 65° C., and the organic condensate is condensed at temperatures from 15° C. to 30° C., b) absorption of methyl mercaptan and dimethyl sulfide from the residual gas stream in an initial wash with methanol and division of the washed, hydrogen sulfide-rich gas stream into a recycle gas stream and a discharge gas stream in a volume ratio of 5:1 to 20:1, c) absorption of hydrogen sulfide from the discharge stream in a second wash with methanol and removal of the cleaned discharge stream from the process, using for the second wash fresh methanol which, after it absorbs hydrogen sulfide, is used as the washing material for the first wash, d) distillation of the charged wash methanol and of the aqueous and organic condensates to thereby separate hydrogen sulfide as the gaseous head product from the remaining components Of the product gas mixture, which collect in the distillation bottoms as a liquid crude product, and feeding the separated hydrogen sulfide gas to the recycle gas stream or the residual gas stream, and e) separation of the crude product, by further distillations, into the components methyl mercaptan, dimethyl sulfide, dimethyl ether, polysulfides, methanol and water.

BRIEF DESCRIPTION OF THE DRAWINGS

The present invention will be further understood with reference to the accompanying drawings, wherein.

DETAILED DESCRIPTION OF THE INVENTION

Figure 1:
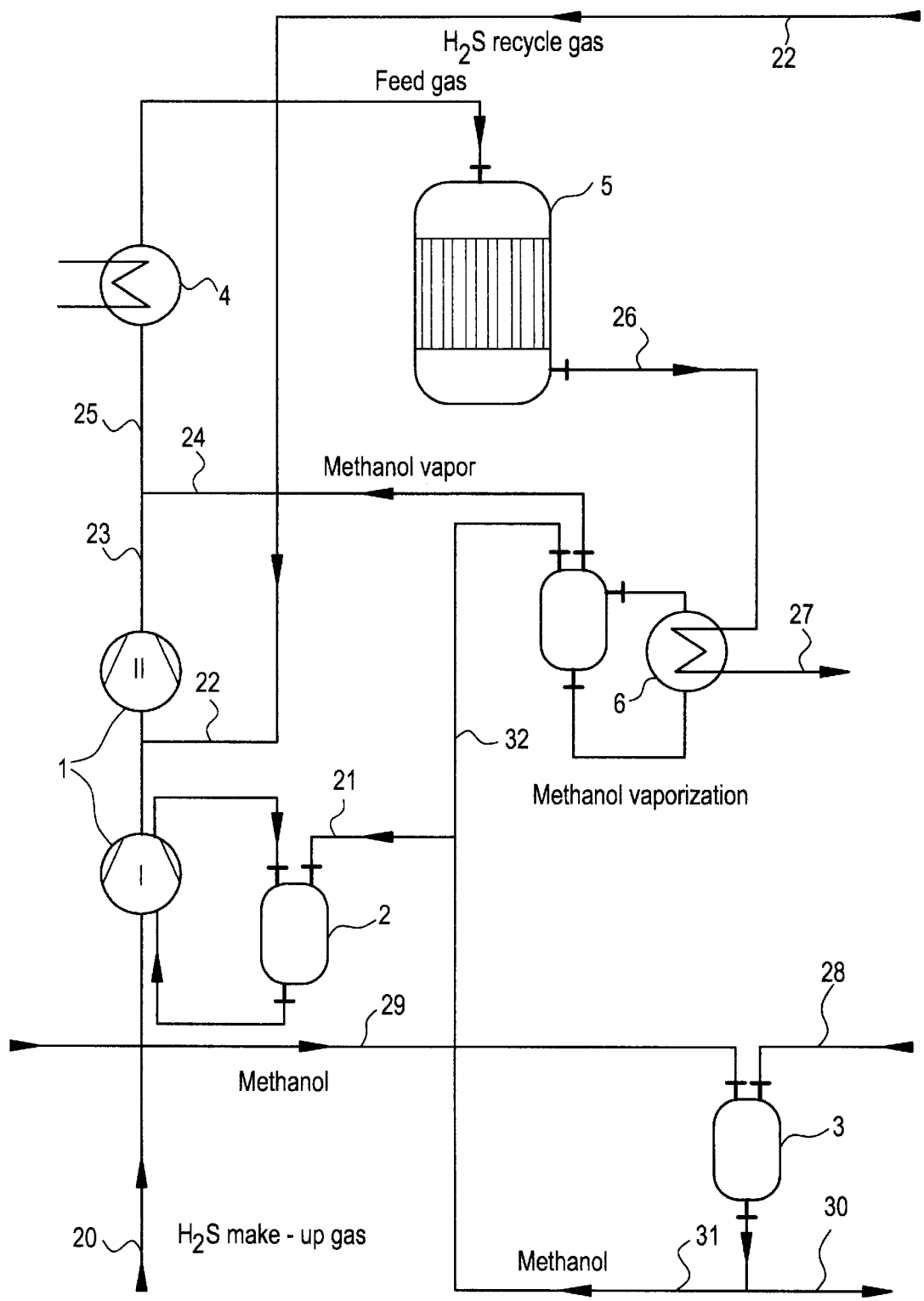
FIG. 1 is a flow diagram for the first part of the methyl mercaptan production process according to the present invention and, FIG. 2 is a flow diagram according to the invention for the second part of the methyl mercaptan production process.

In carrying out the present invention, the product gas mixture from the methyl mercaptan synthesis leaves the reactor at a temperature in the range of 340° C. to 360° C. and a pressure of 6 to 12 bar. It is first cooled to a temperature of about 100° C. to 150° C. for separation into its individual components. That can, for example, be accomplished by heat exchange with hydrogen sulfide, as described in German Patent 17 68 826. Another possibility is to utilize the heat content of the product gas mixture to vaporize methanol, as shown in U.S. patent application Ser. No. 08/885,044, filed Jun. 30, 1997 which is incorporated herein (see the parallel Patent Application attorney docket 96 0139KY, 06-53637).

After the cooling has been done, the product gas mixture is recovered by the process of the invention to separate it into its components and obtain methyl mercaptan.

First, the product gas stream is divided into an aqueous condensate and an organic condensate, as well as a residual gas stream, by two-stage partial condensation. The aqueous condensate consists principally of methanol and water. The principal components of the organic condensate are hydrogen sulfide, methyl mercaptan, and dimethyl sulfide, while the residual gas stream contains hydrogen sulfide and methyl mercaptan as its principal components. The aqueous condensate is separated from the product gas stream at a temperature in the range of 55° C. to 65° C. The organic condensate is obtained in the temperature range of 15° C. to 30° C.

Because of the relatively large temperature difference between the cooling water and the condensation temperature of the aqueous condensate, the heat of condensation of water and methanol can be removed from the product gas stream with relatively small heat exchange areas and small volumes of cooling water.

The residual gas stream remaining after condensation of the aqueous and organic condensates is washed with methanol to absorb methyl mercaptan and dimethyl sulfide. After this initial methanol wash, the residual gas stream contains more than 90% by volume hydrogen sulfide. The remaining volume consists essentially of the inert gases carbon dioxide, carbon monoxide, hydrogen and nitrogen. The actual composition of the washed gas stream depends primarily on the purity of the hydrogen sulfide make-up gas used, which is introduced into the overall process of methyl mercaptan production in the first step of the process. The proportion of the inert gases due to decomposition of methanol in the catalytic conversion to methyl mercaptan can be influenced only slightly by the process parameters of the reaction.

The inert gases must be discharged from the process continuously to avoid accumulation in the overall process of methyl mercaptan production. For that purpose, the washed residual gas stream is divided into a recycle gas stream and a discharge stream in the volume ratio of 5:1 to 20:1. The volume ratio of 5:1 is used when the hydrogen sulfide make-up gas has a high inert gas content. With highly pure hydrogen sulfide the volume ratio can be increased to 20:1.

The recycle gas stream is returned to the first process step. The discharge stream is freed of hydrogen sulfide, according to the invention, by a second washing with methanol. After the washing, the purified discharge stream contains less than 0.1% by volume hydrogen sulfide, and can be taken directly to the waste gas burner. The exhaust gas produced can be discharged directly to the atmosphere in conformity to the currently applicable exhaust gas standards.

This fact distinguishes the process according to the invention from the conventional processes known as the state of the art. According to French Patent 2 477 538, the discharge stream contains more than 70% by volume hydrogen sulfide. Similarly, the discharge stream from the process described in German Patent 17 68 826 also consists predominantly of hydrogen sulfide. Because of that, a valuable raw material is lost from the conventional process representing the present state of the art. Furthermore, the high hydrogen sulfide content of the discharge gas in the conventional processes required suitable measures to remove sulfur dioxide from the exhaust gas if it is burned.

One special feature of the process according to the invention is that both methanol washes are carried out with the same methanol stream. The fresh washing methanol is used first to wash the discharge stream. In that process the wash methanol absorbs hydrogen sulfide. Then the methanol stream carrying hydrogen sulfide is used to wash the residual gas stream, absorbing the methyl mercaptan and dimethyl sulfide which it contains. It has been found that the preloading of the wash methanol with hydrogen sulfide has no negative effects on its capacity to absorb methyl mercaptan.

The hydrogen sulfide and methyl mercaptan are preferably absorbed from the discharge stream or from the residual gas stream isothermally at a temperature in the range of 20° C. to 30° C. To do so, the heat of absorption must be removed by appropriate cooling of the stream of washing material.

The sequential isothermal absorptions of hydrogen sulfide and methyl mercaptan yields substantial saving of washing methanol and gives a discharge stream largely free of hydrogen sulfide. While 2.5 kg methanol per kilogram of methyl mercaptan is required for washing in German Patent 17 68 826, the process according to the invention operates with one-third that quantity.

The wash methanol, and both condensates from the partial condensation, contain high proportions of hydrogen sulfide (wash methanol: 15–20% by weight $H_2S$; aqueous condensate: 1–2% by weight; organic condensate: ca. 20% by weight $H_2S$). The three material streams are distilled together to remove the hydrogen sulfide, so that hydrogen sulfide is removed as the gaseous head product from the remaining components of the product gas mixture. The separated hydrogen sulfide is fed to the recycle gas stream. Aside from hydrogen sulfide, the gaseous head product can still contain substantial proportions of methyl mercaptan. As a result, the recycle gas returned to the first process step can contain up to 3% by volume methyl mercaptan. This methyl mercaptan content can be reduced to less than 1% by volume if the gaseous head product is not fed directly to the recycle gas steam but is instead taken to the first methanol wash along with the residual gas stream.

The liquid still bottoms, or the crude product, from the hydrogen sulfide separation, is separated by further distillations into the components methyl mercaptan, dimethyl sulfide, dimethyl ether, polysulfides, methanol and water.

It is preferable to remove methyl mercaptan and the byproducts, dimethyl sulfide and dimethyl ether, from the methanol and water in the crude product first. Because of the azeotropic mixtures of methyl mercaptan/methanol and dimethylsulfide/methanol in the crude product, an extractive distillation with water as the extractant is used first to break the azeotropes. In this process, methyl mercaptan and dimethyl sulfide appear as the head product, while methanol and water make up the distillation residue. Azeotropic transfer of methanol into the head product is prevented by use of the extraction water. It is also found that no additional reflux is required to concentrate the head product. Instead, it can be taken directly to the subsequent isolation of methyl mercaptan without intermediate condensation. The extraction water is used as the reflux in the extractive distillation.

The head product from the extractive distillation can be separated by another distillation into a head condensate containing methyl mercaptan and water and a still residue consisting essentially of dimethyl sulfide. The head condensate is separated into highly pure methyl mercaptan and water by a liquid—liquid phase separation.

The residue from the extractive distillation contains about equal proportions of methanol and water, minor proportions of low-boilers (methyl mercaptan, dimethyl ether), as well as dimethyl sulfide, and polysulfides. The distillation residue can be redistilled to recover methanol and recycle it into the overall process. In that case, methanol is condensed in the head and reused as wash methanol and for methyl mercaptan synthesis. Water and polysulfides occur in the still bottoms.

Preferably, part of this process water (about ⅔ of the still bottoms) is reused as extraction water in the extractive distillation. The other third, corresponding to the water formed in the reaction, is discharged from the process. To prevent accumulation of polysulfides in the process, and to reduce the odor content of the discharge water, the polysulfides are driven out of the process water with steam and taken to a waste gas burner.

Separation of the product gas mixture according to the process of the invention is carried out at pressures of 1 to 10 bar to limit the cooling capacities required to condense the various components. The initial process step, which includes the process steps a) to d) described above, is operated with the pressure maintained at 6 to 10 bar, preferably 8 bar. The further separation of the crude product from the hydrogen sulfide separation by extractive distillation and subsequent separation into methyl mercaptan and dimethyl sulfide is done at pressures of 4 to 8 bar, preferably 6 bar. Finally, the separation of methanol and process water is preferably done at the standard pressure of 1 bar.

FIG. 1 shows one possible process flow diagram for the first part of the methyl mercaptan production process. It corresponds to the process diagram of FIG. 1 from the parallel patent application (attorney docket 960139 KY, 06-53637). The feed gas mixture 25 of hydrogen sulfide and methanol, with a molar ratio of hydrogen sulfide to methanol of 1.8 is converted over an aluminum oxide catalyst in reactor 5 at an operating pressure of 10 bar and a reaction temperature of 360° C. to methyl mercaptan and byproducts (dimethyl sulfide, dimethyl ether, polysulfides). The catalyst is doped with 25% by weight cesium tungstate according to Example 2 of German Patent Application 196 39 584 to improve its activity and selectivity.

After the product gas mixture 26 has been cooled to 130° C. it is transported to the second stage of methyl mercaptan production as product stream 27. The heat content of the hot product gas mixture is utilized in heat exchanger 6 to vaporize part of the methanol needed for the catalytic reaction.

The hydrogen sulfide make-up gas 20 needed for the reaction is compressed, with a two-stage screw-type compressor 1, through an intermediate pressure of 6 bar to the final pressure of 11 bar. Highly pure hydrogen sulfide containing more than 99% by weight hydrogen sulfide is used in this example. In the first stage of the compressor, liquid methanol is injected from a buffer tank 2 to limit the temperature. Part of the methanol is vaporized by the heat of compression of the first stage. The unvaporized portion is recycled through buffer tank 2. Vaporized methanol is replaced by the methanol stream 21 from the buffer tank 3. After the first compression stage, the hydrogen sulfide recycle gas 22 returned from the second stage of the process is added to the hydrogen sulfide/methanol mixture. Methanol vapor 24 is added to the compressed gas mixture 23 to adjust the molar ratio of hydrogen sulfide to methanol. The feed gas mixture obtained in this manner is heated to about 170° C. in the gas heater 4, and then introduced to the reactor at a pressure of 10 bar. In the reactor it is heated to the reaction temperature by heat exchange with the heat of reaction being released in the catalyst bed.

The methanol consumed in the reaction is replaced with make-up methanol 29 from the buffer tank 3. The methanol recycled from the second stage of the process is fed to the buffer tank 3. A methanol stream 31 is taken from buffer tank 3 for the catalytic reaction, as well as a methanol stream 30 as wash methanol for the second process stage.

The second stage of the process, which is the subject of this invention is, then, linked with the first stage through the material streams 22 (hydrogen sulfide recycle gas), 27 (product gas mixture), 28 (separated wash methanol) and 30 (make-up wash methanol).

The product gas mixture 27 leaving the first process stage has the following properties in this example:

| | |
|---|---|
| Methyl mercaptan: | 39% by weight |
| Dimethyl sulfide: | 1.6% by weight |
| Dimethyl ether: | 2.7% by weight |
| Inert gases ($H_2$, CO, $CO_2$, $N_2$): | 2.5% by weight |
| Water: | 15% by weight |
| Hydrogen sulfide: | 34% by weight |
| Methanol: | 5% by weight |
| Temtperature: | 130° C. |
| Pressure: | 8 bar |

Figure 2:
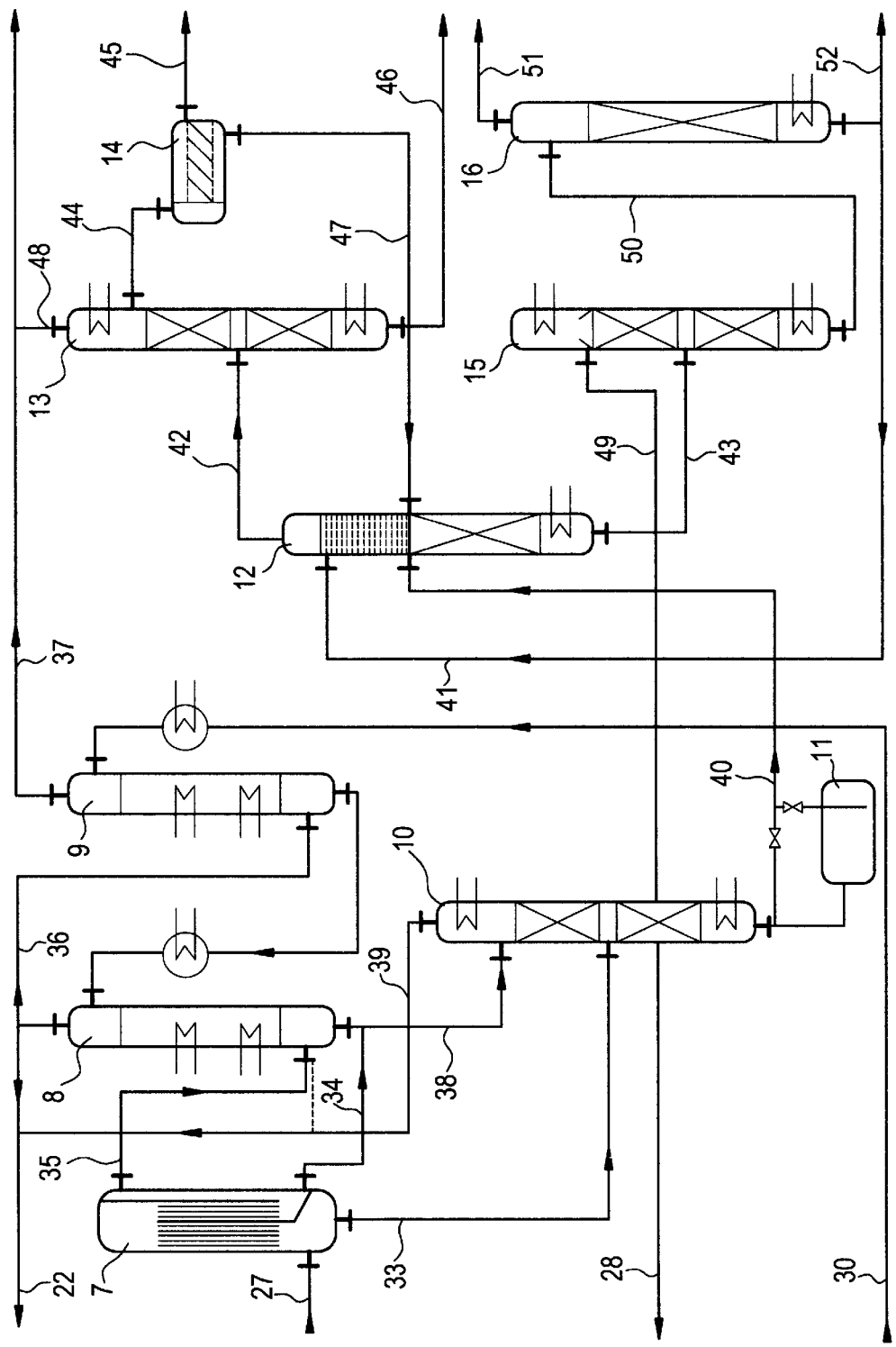

One specific embodiment of the process according to the invention is explained by means of the process diagram of FIG. 2.

Product gas mixture with the properties shown above occurs as a mass flow of 2.7 t/t MM (MM=methyl mercaptan) and is taken to the two-stage partial condenser 7.

In the first condensation stage, the higher-boiling components, methanol and water, are predominantly condensed at a temperature of 60° C. as the aqueous condensate 33. Cooling water at ordinary temperature can be used for cooling. In the second stage, an organic condensate 34, containing about 75% by weight methyl mercaptan, is condensed at 25° C. Here the cooling must be done with cold water at about 5° C. A cooling power of about 180 Kw/t MM is required for the mass flows under consideration here.

The uncondensed residual gas stream 35 still contains, along with hydrogen sulfide as the principal component, about 30% of the methyl mercaptan that was in the product gas stream 27 before condensation. The methyl mercaptan is absorbed from the residual gas stream by a multistage washing with methanol. That is done in the methyl mercaptan absorber 8 (MM absorber). Because of the substantial heat of condensation and heat of absorption, heat exchangers are placed along the column so that the absorption can be carried out isothermally at a preferred temperature of 25° C. The heat of absorption which must be removed is 48 kW/t MM. In this way, methyl mercaptan can be washed out to below 1% by volume. Water at 5° C. can be used as the coolant.

The residual gas stream is introduced to the bottom of the MM absorber and flows upward, countercurrent to the washing liquid, for methyl mercaptan absorption. Methanol is added as the wash liquid at the head of the absorber column at a temperature of 15° C.

The residual gas stream leaving the absorber column is under a pressure of about 6 bar. Its principal component, other than hydrogen sulfide, is 10% by volume inert gas ($H_2$, $CO_2$, $CO$, $N_2$). This residual gas stream is divided, at a volume ratio of 7:1, into a recycle gas stream 22 and a discharge stream 36. The recycle gas is returned to the first step of the process and mixed with the hydrogen sulfide make-up gas before the second stage of compression. The splitting of the discharge gas stream is required to prevent accumulation of the inert gases in the first stage of the process. The volume ratio of 7:1 assures, in this case, that the quantities of inert gases introduced with the hydrogen sulfide make-up gas and formed in the synthesis reactor by decomposition of methanol are removed continuously.

The discharge stream is washed again with methanol in a hydrogen sulfide absorber column ($H_2S$ absorber) to avoid loss of hydrogen sulfide. This wash is also preferably done isothermally at a temperature of 25° C. It is done by introducing the discharge stream from the bottom so that if flows countercurrently to the methanol introduced at the top. The $H_2S$ absorber column is also equipped with cooling elements which remove the heat of absorption, about 18 kW/t MM, so that the absorption can be done isothermally. The purified discharge gas stream 37 leaving the $H_2S$ absorber is almost completely free of hydrogen sulfide (less than 0.1% by volume) and can be taken to the burner.

The same methanol stream is used for the first methanol wash in the MM absorber and the second methanol wash in the $H_2S$ absorber. That is accomplished by taking methanol from the buffer tank 3 as stream 30 (see FIG. 1) and cooling it to 15° C. in a cooler before it is introduced at the head of the $H_2S$ absorber. After absorption of hydrogen sulfide in the $H_2S$ absorber, the wash methanol carried about 15% by weight hydrogen sulfide. After cooling back to 15° C., it is introduced to the head of the MM absorber to absorb the methyl mercaptan from the residual gas stream. In the MM absorber the wash methanol is charged with about 30% by weight methyl mercaptan. The previous loading with hydrogen sulfide does not have a bad effect on the absorption of methyl mercaptan.

Both the condensate streams 33 and 34 from the partial condenser, and the wash methanol 38, contain high proportions of dissolved hydrogen sulfide (aqueous condensate 33: ~1% by weight; organic condensate 34: ~20% by weight; wash methanol 38: ~19% by weight). A stripper column 10 with 10 theoretical plates is used to remove the hydrogen sulfide from these streams. Organic condensate and methanol are added together at the top of the column, while the higher-boiling aqueous condensate is introduced at about half the height of the stripper column. The distillation is done at a pressure of 8 bar. At this pressure, the boiling temperature in the pot is about 85° C.

The hydrogen sulfide leaves the head of the stripper column as the gas stream 39 and is fed into gas stream 22. Gas stream 39 contains, aside from hydrogen sulfide, some of the low-boiling components, methyl mercaptan, dimethyl ether, and dimethyl sulfide. To improve the sharpness of the separation, a partial condenser which limits the methyl mercaptan content of the gas stream 39 to less than 10% by volume at a selected condensation temperature of 25° C. can be integrated into the head of the stripper column.

As an alternate to feeding into the recycle gas stream 22, the gas stream 39 can also be combined with the residual gas stream 35 in the MM absorber (see the connection indicated by the dot-dash line). That reduces the concentration of methyl mercaptan in the recycle gas stream. When stream 39 is fed directly into the recycle gas stream, the recycle stream contains less than 3% by volume methyl mercaptan. If stream 39 is routed through the MM absorber the methyl mercaptan content of the recycle gas stream can be reduced to less than 1% by volume.

A "crude product" appears in the distillation sump of the stripper column. It has the following composition:

| | |
|---|---|
| Methyl mercaptan: | 43% by weight |
| Dimethyl sulfide: | 2% by weight |
| Dimethyl ether: | 2% by weight |
| Methanol: | 34.7% by weight |
| Water: | 18% by weight |
| Higher sulfides: | less than 0.5% by weight |

It is collected in buffer tank 11 after cooling to about 60° C. From there it is fed to the appropriate temperature level of a preseparator column 12, where it is separated into a stream containing methyl mercaptan and dimethyl sulfide, and another stream containing methanol and water. An extractive distillation process is used in the preseparator column to separate the azeotropic mixtures in the crude product. Water, which is added at the head of the preseparator column, is used as the extractant. The working pressure in the preseparator column is 6 bar. The head product from the preseparator column contains:

| | |
|---|---|
| Methyl mercaptan: | ~93% by weight |
| Dimethyl sulfide: | ~4.5% by weight |
| Dimethyl ether: | ~1.5% by weight |
| Water: | ~1% by weight |
| Methanol: | Traces |

It is preferably transported as stream 42 without intermediate condensation to another distillation in the "pure product column". The vapor stream 42 is introduced at about the middle of the pure product column, which also operates at 6 bar. Methyl mercaptan and dimethyl sulfide are separated in the pure product column. Methyl mercaptan appears as the head product and is condensed in an integrated condenser, in which the reflex is produced at the boiling temperature and then the product is withdrawn by subcooling. The head condensate which leaves at the head of the pure product column is separated into methyl mercaptan and water in the water separator 14 after further cooling to 20° C. The pure product column is blanketed with an inert gas 48, preferably nitrogen, at a pressure of 6 bar to compensate for pressure fluctuations.

Methyl mercaptan at high purity is removed from the water separator as stream 45. It has approximately the following composition:

| | |
|---|---|
| Methyl mercaptan: | ~98% by weight |
| Diiuethyl sulfide: | 0.1% by weight |
| Dimethyl ether: | 1.5% by weight |
| Water: | 0.37% by weight |
| Methanol: | 0.03% by weight |
| Hydrogen sulfide: | Traces |

The water separated can be fed to the preseparator column as stream 47.

The dimethyl sulfide which is found in the bottoms of the pure product column is also of high purity and is marketable. The stream 46 (dimethyl sulfide) is about 2% of stream 45 (methyl mercaptan).

The distillation residue from the preseparator column has approximately the following composition:

| | |
|---|---|
| Methanol: | ~43% by weight |
| Water: | ~54.5% by weight |
| Sulfide-containing byproducts: | ~1% by weight |
| Dimethyl ether: | ~1% by weight |

The methanol portion is made up of the wash methanol (stream 30) (~85% by weight) and the methanol not completely converted in the catalytic synthesis. The water portion is derived from the extraction water (stream 41) and the water produced in the synthesis reaction. The sulfide-containing byproducts, principally dimethyl sulfide, are also produced in the synthesis.

For recovery of the valuable methanol, the distillation residue from the preseparator column is depressurized from 6 to 1 bar and taken as stream 43 to a methanol/water separation column. Methanol is removed at the head of the column. The process water appears as the bottoms, and contains small quantities of polysulfides.

In this methanol/water separation column both the water concentration in the head product and the methanol concentration in the sump can be limited to 0.2% by weight.

The methanol withdrawn at the head of the column is returned to buffer tank 3 as stream 49 or stream 28 (see FIG. 1) and reused as washing methanol and synthesis methanol. It contains not more than 0.5% by weight dimethyl sulfide.

Part of the process water which appears at the bottom of the methanol/water separation column, equivalent to the reaction water produced in the synthesis, must be discharged continuously from the process. The other part, amounting to about two thirds of the process water, is introduced to the preseparator column as extraction water 41. To prevent both accumulation of polysulfides in the extraction water and excessive odor in the reaction water to be discharged, the process water is introduced into the head of a stripper column. Steam is generated in the column pot and is directed countercurrently to the process water. Because of the heteroazeotropic properties of the polysulfides, they are removed with the steam. Only about 5% of the process water is needed as steam to drive the polysulfides off completely. The head stream from the stripper column, enriched with polysulfides, can be burned without other treatment. The process water leaving the stripper column as the bottoms is nearly odor-free.

Further variations and modifications of the foregoing will be apparent to those skilled in the art and are intended to be encompassed by the claims appended hereto.

German priority application 196 54 516.1 is relied on and incorporated herein.

We claim:

1. A process for the dividing of a product gas mixture obtained from the catalytic synthesis of methyl mercaptan from hydrogen sulfide and methanol, which is at a temperature of 100° C. to 150° C. and a pressure of 6 to 12 bar, into the component methyl mercaptan, dimethyl sulfide, polysulfides, water, methanol, hydrogen sulfide and inert gases, comprising:

a) dividing a product gas stream into an aqueous condensate containing methanol and water and into an organic condensate containing hydrogen sulfide, methyl mercaptan and dimethyl sulfide, and into a residual gas stream containing hydrogen sulfide and methyl mercaptan, by a two-stage partial condensation in which the aqueous condensate is condensed at temperatures from 55° C. to 65° C., and the organic condensate is condensed at temperatures from 15° C. to 30° C., b) absorbing methyl mercaptan and dimethyl sulfide from the residual gas stream in an initial wash with methanol and dividing the washed, hydrogen sulfide-rich gas stream into a recycle gas steam and a discharge gas stream in a volume ratio of 5:1 to 20:1, c) absorbing hydrogen sulfide from the discharge stream in a second wash with methanol and removing of the resulting cleaned discharge stream from the process, using for the second wash fresh methanol which, after it absorbs hydrogen sulfide, is used as the initial wash in (b) and, d) distilling the methanol and the aqueous and organic condensates to separate hydrogen sulfide as the gaseous head product from the remaining components of the product gas mixture, collecting in the distillation bottoms as a liquid crude product, and feeding the separated hydrogen sulfide gas to the recycle gas stream or the residual gas stream.

2. The process according to claim 1 further comprising dividing the crude product, by further distillations, into the components methyl mercaptan, dimethyl sulfide, dimethyl ether, polysulfides, methanol and water.

3. The process according to claim 1, wherein the absorping of hydrogen sulfide and methyl mercaptan by washing with methanol is done isothermally at a temperature in the range of 20° C. to 30° C.

4. The process according to claim 1, wherein the crude product, which contains the azeotropic mixtures methyl mercaptan/methanol and dimethyl sulfide/methanol is divided by extractive distillation into a stream containing methyl mercaptan and dimethyl sulfide and a stream containing methanol and water, with water being used as the extractant, where methyl mercaptan and dimethyl sulfide appear as the head product and methanol and water as the distillation residue.

5. The process according to claim 4, wherein the stream containing methyl mercaptan and dimethyl sulfide is divided by distillation into a head condensate containing methyl mercaptan and water and a bottoms product containing dimethyl sulfide, and that the head condensate is separated by a liquid—liquid phase separation into methyl mercaptan of high purity and water.

6. The process according to claim 4 wherein, the distillation residue containing methanol and water is further distilled whereby methanol is condensed at the head and recycled and for the methyl mercaptan synthesis, and water, still containing a low proportion of polsulfides, appears as the bottoms product.

7. The process according to claim 6, wherein polysulfides in the water are driven off with steam and taken to a waste gas burner.

8. The process according to claim 7, wherein part of the water purified of polysulfides, equivalent to the reaction water produced in the synthesis process, is discharged and the rest of the water that is not discharged is returned to the extractive distillation as extraction water.

9. The process according to claim 5 wherein, the stream containing methyl mercaptan and dimethyl sulfide is divided by distillation into a head condensate containing methyl mercaptan and water and a bottoms product containing dimethyl sulfide, and that the head condensate is separated by a liquid—liquid phase separation into methyl mercaptan of high purity and water.

10. The process according to claim 1 wherein the cleaned discharge stream of (c) contains less than 0.1% by volume $H_2S$.

* * * * *